United States Patent [19]

Rausch

[11] Patent Number: 4,766,224

[45] Date of Patent: Aug. 23, 1988

[54] PURIFICATION AND ACTIVATION OF PROTEINS FROM INSOLUBLE INCLUSION BODIES

[75] Inventor: Steven K. Rausch, Terre Haute, Ind.

[73] Assignee: International Minerals & Chemical Corp., Terre Haute, Ind.

[21] Appl. No.: 767,032

[22] Filed: Aug. 19, 1985

[51] Int. Cl.$^4$ ................................................ C07K 3/28
[52] U.S. Cl. .................... 530/412; 530/416; 530/417; 530/422; 530/399; 530/825; 435/68
[58] Field of Search .............. 260/112 R; 435/68, 70; 530/412, 416, 417, 422, 426, 825, 399

[56] References Cited

U.S. PATENT DOCUMENTS

| 4,426,323 | 1/1984 | Jain | 435/68 |
| 4,462,940 | 7/1984 | Hanisch et al. | 424/85 |
| 4,511,502 | 4/1985 | Builder | 260/112 R |
| 4,511,503 | 4/1985 | Olson | 260/112 R |
| 4,518,526 | 8/1985 | Olson et al. | 260/112 R |
| 4,599,197 | 7/1986 | Wetzel | 435/70 |
| 4,677,196 | 6/1987 | Rausch | 530/412 |

OTHER PUBLICATIONS

Protein Purification, Ed. Scopes, Ion Exchange Chromatograph, 1982, pp. 81-82.

Primary Examiner—John Kight
Assistant Examiner—Garnette D. Draper
Attorney, Agent, or Firm—Wendell R. Guffey; Thomas L. Farquer; Peter R. Shearer

[57] ABSTRACT

Purification and solubilization of proteins produced in transformant microorganisms as insoluble, biologically inactive inclusion bodies is effected by solubilizing the inclusion bodies in SDS; treating the SDS-protein solution with urea; removing the SDS and purifying the protein by chromatography on an anion-exchange resin having cationic groups attached to a polysaccharide support; and dialyzing the solution obtained from the anion-exchange resin to remove urea, thereby allowing the protein to fold into its native conformation. The solution thus obtained can be activated by removing soluble protein aggregates via ultrafiltration or chromatography on a weak anion-exchange column.

25 Claims, No Drawings

PURIFICATION AND ACTIVATION OF PROTEINS FROM INSOLUBLE INCLUSION BODIES

BACKGROUND OF THE INVENTION

This invention relates to methods for purifying and activating proteins that are produced as insoluble, biologically inactive inclusion bodies in microorganisms that have been transformed with recombinant DNA expression vectors to direct expression of the protein of interest.

Recombinant DNA technology allows the insertion of a vector carrying foreign (heterologous) DNA into a microorganism in a manner which allows the heterologous DNA to be expressed; that is, the vector contains genetic instructions which direct the microorganisms to produce a protein which is encoded by a portion of the heterologous DNA sequence. By growing transformant microorganisms in a fermentor and subjecting them to conditions under which the heterologous DNA is expressed, valuable proteins can be produced in large quantity at relatively low cost.

Unfortunately, many heterologous proteins which are produced in transformant microorganisms do not fold into their native three-dimensional conformation in the host cell environment. This improper folding of the expressed protein has several untoward consequences. In the first place, the improperly folded proteins tend to form aggregates which are insoluble within the host cell. These insoluble aggregates are recognizable within the cell as "inclusion bodies", sometimes also referred to as "refractile bodies" and/or "protein granules." The formation of inclusion bodies may also be partially caused by oligomerization of the protein, that is, the formation of covalent intermolecular disulfide bonds. Not only are the improperly folded proteins insoluble, but also they are biologically inactive. As exemplary of heterologous proteins which form insoluble, biologically inactive inclusion bodies upon expression in a host cell, one can mention animal growth hormones and growth factors such as bovine growth hormone, swine growth hormone and somatomedin.

In order to produce useful proteins, it is necessary to convert the improperly folded inclusion body proteins into their native conformations, in which they are soluble and biologically active. Moreover, it is necessary to purify the protein in order to remove contaminating cell debris and host cell proteins. A number of schemes have been proposed for converting inclusion body proteins into their soluble, native configurations. Unfortunately, these schemes are often incompatible with protein purification procedures, such as ion-exchange chromatography. The conditions of purification tend to inhibit the ability to maintain the protein in solution, often resulting in a substantial loss of protein due to reaggregation and precipitation. Consequently, most of the schemes proposed for recovering proteins from inclusion bodies in purified, soluble, biologically active form have resulted in very low yields of the protein produced by the microorganisms.

U.S. Pat. No. 4,511,503 discloses a typical scheme for recovering proteins from inclusion bodies in transformant microorganisms. The inclusion body proteins are treated with a strong denaturant, which causes the improperly folded protein molecules to unfold and become soluble. The denaturant is subsequently removed, for example, by dialysis, in order to allow the protein to refold into its native conformation. The most commonly employed strong denaturant in schemes of this type has been guanidine hydrochloride.

U.S. Pat. No. 4,511,502 discloses a similar process wherein the solubilized protein/denaturant solution is passed over a molecular sieve or centrifuged at high speed to remove higher molecular weight components.

U.S. Pat. No. 4,518,526 also discloses a similar process. In this process, the transformant cell culture is treated with a buffered solution of sufficient ionic strength to solubilize most of the host cell protein, whereas the heterologous protein remains insoluble. The cells are then lysed, the supernatant containing the solubilized host cell protein removed and the insoluble inclusion bodies solubilized in the strong denaturant.

Other publications disclosing denaturation/renaturation schemes for converting inclusion body proteins into their soluble, native conformations include PCT publication WO No. 83/04418, European Patent Application Publication No. 0 123 928, European Patent Application Publication No. 0 121 775, European Patent Application Publication No. 0 116 778 and European Patent Application Publication No. 0 114 507.

As previously indicated, most of the proposed denaturation/renaturation schemes have employed guanidine hydrochloride as the denaturant. While guanidine hydrochloride is characterized by an excellent ability to solubilize inclusion body proteins, its use entails some problems. Upon dialysis against denaturant-free buffer to remove the guanidine hydrochloride, a substantial amount of the solubilized protein reaggregates, apparently due to improper refolding. Moreover, when guanidine-solubilized protein is purified by methods such as ion-exchange chromatography—which are necessary to obtain the degree of purity required in the final product—very substantial losses of protein are incurred due to reaggregation. Fouling and plugging of the column tends to occur in an inordinately short time, severely limiting the useful life of the column. Typically, we have found that guanidine solubilization of bovine growth hormone inclusion bodies, followed by ion-exchange chromatography yielded only 4–12% product recovery.

Another major problem associated with the use of guanidine hydrochloride—one which is particularly important from a commercial production standpoint—is its high cost. It would be highly desirable to employ a solubilizing agent which is comparable to guanidine hydrochloride in its ability to solubilize inclusion body proteins, but without the associated high cost of guanidine. U.S. Pat. No. 4,511,503 suggests the use of detergents such as sodium dodecyl sulfate (SDS) as denaturants. However, there is no demonstration of its use, nor is there a proposal for a method to remove the detergent from the protein and purify the protein.

Detergents such as SDS are highly effective denaturing agents. Moreover, SDS is a much less expensive reagent than guanidine hydrochloride. Accordingly, its potential use in recovering inclusion body proteins is attractive from the standpoint of commercial production economics. Compared with guanidine hydrochloride, however, SDS binds to the denatured protein much more tightly, making its complete removal from the protein problematical.

O. H. Kapp and S. W. Vinogradov demonstrated that SDS could be removed from several proteins by chromatography on the ion-retardation resin AG11A8

(*Anal. Biochem.*, 91:230–233 [1978]). It was said that from 0.1 to 1.4 moles of SDS remained on each mole of protein treated in this manner. K. Weber and D. J. Kuter demonstrated that SDS could be removed from aspartate transcarbamylase by incubation in urea and subsequent anion-exchange chromatography (*J. Biol. Chem.*, 246:4504–4509 [1971]). In both instances, however, the starting proteins were in pure, biologically active form. There is no suggestion of a method for efficiently recovering protein in a pure, biologically active form from insoluble, intracellular inclusion bodies.

SUMMARY OF THE INVENTION

This invention provides an efficient, economical method for recovering and purifying proteins that are produced as insoluble, biologically inactive inclusion body proteins in transformant microorganisms. The method of the invention converts the protein into its soluble, native conformation and concomitantly purifies the protein. In the method of the invention, a detergent such as SDS is used as a denaturant, rather than a more expensive denaturant such as guanidine hydrochloride. Using SDS as the denaturant in accordance with the method of the invention, we have obtained recovery yields of up to 17%, based on the amount of protein present in the inclusion bodies. These yields are as good as or better than those obtainable with prior processes using guanidine hydrochloride as the denaturant. The protein product obtained by the method of the invention is soluble, essentially homogeneous and essentially free of SDS.

In particular, the invention provides a method for purifying and recovering in soluble form a protein that is produced as an insoluble, impure inclusion body in a transformant microorganism which comprises:

(a) extracting the inclusion body into a buffered solution of sodium dodecyl sulfate to solubilize the protein;

(b) treating the solution of sodium dodecyl sulfate and protein with urea;

(c) removing the sodium dodecyl sulfate and purifying the protein by chromatographing the solution obtained in step (b) on an anion-exchange column; and (d) dialyzing the protein solution obtained from the anion-exchange column to remove urea, thereby allowing the protein to fold into its native conformation.

The solution of pure, soluble protein obtained from step (d) can be activated by removing soluble protein aggregates from the solution. Soluble protein aggregates conveniently can be removed by ultrafiltration or by chromatography on a weak anion-exchange column.

DETAILED DESCRIPTION OF THE INVENTION

The method of the invention is used to purify and activate proteins which are produced in the form of insoluble, biologically inactive inclusion bodies in transformant microorganisms, i.e., microorganisms which have been transformed with recombinant DNA vectors that direct the expression of genes coding for heterologous proteins. Generally, the proteins which can be purified and activated by the method of the invention are negatively charged proteins which are basic under the processing conditions that are described below in detail. In specific embodiments of the invention, the proteins which are purified and activated are animal growth hormones such as bovine growth hormone (bGH) or porcine growth hormone (pGH).

It is to be understood that reference herein to proteins generally—e.g., hormones and enzymes—or to specific proteins such as bGH and pGH is not intended to be restricted to molecules which contain the full amino acid sequence of the natural protein. Rather, it is also intended to include fragments of the protein having various portions of the sequence deleted and proteins or fragments thereof having various substitutions or modifications in their natural sequences which do not destroy the biological activity of the molecules.

The genes for bGH and pGH have been cloned onto expression vectors and used to transform *E. coli* host cells. European Patent Application Publication No. 0 103 395 describes the construction of a transformant strain of *E. coli* containing a first plasmid which codes for Δ9(Ser)bGH (bGH less its 9 N-terminal amino acids and having an additional serine residue at the N-terminus) under the control of the $\lambda P_L$ promoter-operator and which has a Shine-Dalgarno region derived from bacteriophage mu. The transformant also contains a second plasmid, pcI857, which codes for the production of the cI857 temperature-sensitive repressor protein. The repressor protein can be inactivated by raising the temperature to about 42° C., thereby inducing expression of Δ9(Ser)bGH. A transformant strain of this type, *E. coli* HB101 ($P_L$-mu-Δ9(Ser)bGH and pcI857) has been deposited, with the designation *E. coli*, IMC No. 1, at The American Type Culture Collection, Rockville, Md., with accession No. 53030.

Construction of a similar transformant strain which codes for the production of Δ7pGH (porcine growth hormone less its first 7 N-terminal amino acids) is described in European Patent Application Publication No. 0 104 920. A transformant strain of this type, *E. coli* HB101 ($P_L$-mu-Δ7pGH and pcI857) has been deposited, with the designation *E. coli*, IMC No. 2, at The American Type Culture Collection, Rockville, Md., with accession No. 53031.

*E. coli*, IMC No. 1 and *E. coli*, IMC No. 2 are prolific producers of Δ9(Ser)bGH and Δ7pGH, respectively. In both instances, the expressed protein is sequestered within the cell in the form of insoluble, biologically inactive inclusion bodies which are visible under a microscope.

After the transformant cells have been grown in a fermentor and the protein of interest has been expressed and allowed to accumulate within the cells as inclusion bodies, the transformant cells are generally lysed, either mechanically, chemically or enzymatically, to allow isolation of the inclusion bodies which are sequestered within the cells. Prior to employing the method of the invention, the inclusion bodies can be separated from the bulk of the remainder of cellular material by centrifugation and washing in a buffer to produce a wet inclusion body paste.

The inclusion bodies are extracted into a buffered solution of SDS to solubilize the protein. The amount of sodium dodecyl sulfate in the buffered solution is an amount sufficient to dissolve the protein. Preferably, the buffered solution contains from about 0.5% to 5.0% sodium dodecyl sulfate, most preferably about 1%. We have found that high pH buffer solutions, i.e., from about pH 8.5 to pH 10.5 are best suited to maintaining the protein in a solubilized form. A suitable SDS buffer solution is 0.01 to 0.1 M ethanolamine-HCl. If desired, the SDS solution can also contain reducing agents such as 2-mercaptoethanol in amounts sufficient to prevent the formation of intermolecular disulfide bonds during the recovery procedure. We have not found, however, that the presence of reducing agents significantly improved the yield of recovered soluble protein. Disaggregation of the inclusion bodies in the SDS solution generally occurs over a period of about 4 to 18 hours.

After the inclusion body proteins have been solubilized in the SDS solution and the protein allowed to disaggregate, the protein solution is treated with urea. The treatment with urea is essential to the achievement of complete removal of SDS from the protein in the subsequent anion-exchange chromatography step. In the absence of urea, the SDS-protein complex binds to the anion-exchange column in a manner which makes it impossible to elute the protein free of SDS.

Urea can be aded directly to the SDS-protein solution, in the form of solid urea to a concentration from about 4 M to about 10 M, preferably about 6 M. The urea-treated SDS-protein solution can be adjusted, if necessary, to a pH from about pH 7.5 to about pH 9.5, preferably about pH 9.0, prior to the chromatography step. Advantageously, however, the buffer is selected such that no pH adjustment is required.

The urea-treated SDS-protein solution is subjected to anion-exchange chromatography to remove SDS from the protein and concomitantly to purify the protein. The resin on which the solution is chromatographed is preferably a strong anion-exchange resin having cationic groups attached to a polysaccharide support. A polysaccharide support is preferred because supports such as polystyrene or copolymers thereof (e.g., supports such as Dowex AG1-X2) may interact with the protein and interfere with the separation of protein and SDS. Any of the known polysaccharide supports commonly used in ion-exchange resins may be employed such as, for example, beads of dextran, agarose or cellulose. Additionally, synthetic resins which are known to be compatible with protein purification can also be employed as solid supports. One such resin is known as Trisacryl.

Those skilled in the art will recognize that the term "strong anion-exchange resin" refers to resins having cationic groups which maintain their positive charge at relatively high pH, e.g., above pH 9.0. The cationic groups attached to the support may be selected from quaternary ammonium groups, such as $-CH_2CH_2N^+(CH_2CH_3)_2CH_2CH(OH)CH_3$. One can mention as examples of suitable commercially available anion-exchange resins for use in the practice of the invention QAE-Sephadex A-25, QE-52 cellulose, Cellex QAE, and Q-Sepharose Fast Flow.

The anion-exchange resin is usually employed in the form of a packed column. The column is equilibrated using conventional techniques and the urea-treated SDS-protein solution is loaded onto the column. The protein is eluted under eluting conditions in which the SDS remains bound to the resin. Typically, the protein is eluted from the column using an eluent selected from buffered solutions of 4-8 M urea at alkaline pH (e.g., 8.5-10.5). Upon elution of the protein, SDS and contaminating protein remains bound to the column. The column can be regenerated by washing with solutions of NaOH and nonionic detergents to remove SDS and contaminating protein and equilibrating the column.

The protein which is eluted from the anion-exchange column remains in a soluble, unfolded state due to the presence of urea, which is a denaturing agent. In order to refold the protein into its native configuration, thereby imparting biological activity, the urea must be removed from the solution. This is accomplished by dialyzing the solution. Normally, the protein-urea solution will be dialyzed against several volumes of buffered, urea-free solution. If desired, however, removal of urea can be accomplished by sequential dialysis steps against increasingly dilute solutions of urea.

As used herein, the term "dialysis" refers to any technique in which urea is removed from the protein solution by selective transport of urea across a semi-permeable membrane with retention of the desired protein molecules on the other side of the membrane. Any of the known methods of dialysis may be used with a variety of types of equipment. For example, urea may be dialyzed from the solution using hollow fiber ultrafiltration systems. In these systems, a urea-free buffer solution of low ionic strength is circulated around bundles of semi-permeable hollow fibers. Small molecules in the protein solution that flows through the fibers are capable of passing through the membranous fiber wall so as to reduce the urea concentration of the protein solution. Other known dialysis techniques including, but not limited to diafiltration and sack dialysis can also be employed to remove urea from the protein solution. The dialyzate contains protein, e.g., bGH or pGH, which is soluble, essentially homogeneous and essentially free of SDS and urea.

After each of the steps described above, i.e., after extraction into SDS, anion-exchange chromatography and dialysis, the protein-containing solution can be clarified, e.g., by centrifugation, to remove any precipitates which may have formed and the precipitates can either be discarded or recycled.

The purified, soluble protein obtained by the procedures described above usually has a relatively low level of biological activity due to the presence of inactive soluble protein aggregates. Therefore, it is desirable to activate further the protein solution by removing soluble protein aggregates. This can be conveniently achieved by ultrafiltration or by chromatography on a weak anion-exchange resin.

If removal of the soluble protein aggregates is effected by ultrafiltration, the cut-off point of the ultrafiltration membrane is selected to allow passage of the desired protein in monomeric form while retaining protein aggregates on the other side of the membrane. In the case of bGH or pGH, we employ a membrane having a cut-off point of 100,000 daltons. While this is substantially greater than the molecular weight of the desired protein monomer, we have found that protein deposition on the membrane during operation of the ultrafiltration unit effectively lowers the cut-off point.

Weak anion-exchange resins which can be employed to remove protein aggregates from the solution are resins having attached cationic groups which lose positive charge at relatively high pH, e.g., above pH 9.0. Typically, the cationic groups in weak anion-exchange resins are diethylaminoethyl (DEAE) groups. Preferred solid supports are polysaccharide supports, as previously exemplified, or synthetic resins which are compatible with protein purification, such as Trisacryl. A preferred weak anion-exchange resin is DEAE-Trisacryl.

The weak anion-exchange resin is normally employed in the form of a packed column. The solution containing the purified, soluble protein (monomer and aggregates) is loaded onto the column under conditions in which the protein aggregates bind to the column but the monomers do not bind. The biologically active monomer is collected in the pass-through fraction. Preferably, the protein solution is loaded onto the column at pH 9.0 to 10.0. Under these conditions, the column is weakly positively charged, so that the protein aggregates, but not the monomers, are bound.

Using the methods of the invention, we have obtained yields of soluble, biologically active protein of up to 17%. These yields are as good or better than those which have typically been obtained with procedures that use guanidine hydrochloride as a denaturant.

The following examples are intended to illustrate further the practice of the invention and are not intended to limit the scope of the invention in any way.

EXAMPLE I

Purification and Activation of Δ9(Ser)bGH

Inclusion bodies were obtained from *E. coli*, IMC No. 1 (ATCC 53030), which had been cultured under Δ9(Ser)bGH-producing conditions. The cells were centrifuged out of the fermentor beer and resuspended in 0.1 M Tris-HCl, pH 7.8, 10 mM EDTA, 5% sucrose. Lysozyme was added at 200 mg/liter and incubated at 28° C. for 40 minutes, at which time the cells were again centrifuged out. They were resuspended in 0.1 M phosphate buffer, pH 7.8 containing 10 mM EDTA, and 0.5 mM reduced glutathione and lysed by passing twice through a Manton-Gaulin homogenizer at 6000-8000 psi. Phenylmethylsulfonyl fluoride was added as a protease inhibitor at a concentration of 0.5 mM and the crude inclusion bodies were centrifuged out. The pellet was washed three times by resuspension in 0.1 M Tris-HCl, pH 7.8, 2 M urea, 1% Triton X-100, 0.5 mM dithioerythritol (DTE) followed by centrifugation. The remaining pellet was washed twice more with 0.1 M Tris-HCl, pH 7.8, 0.5 mM DTE.

Two grams of these inclusion bodies were extracted with 20 volumes of 60 mM ethanolamine-HCl, pH 9.8, 1% SDS, by stirring vigorously for 24 hours. The resulting extract was dialyzed against 30 volumes of 60 mM ethanolamine-HCl, pH 9.0. Solid urea was then added to a final concentration of 6 M. After incubating at room temperature for 2 hours, 40 ml of the treated extract were loaded onto a 2.5×20 cm column of QAE-Sephadex A-25 equilibrated in 60 mM ethanolamine-HCl, pH 9.0, 6 M urea. The Δ9(Ser)bGH eluted in the void volume of the column. The relevant fractions were pooled and dialyzed against 60 mM ethanolamine-HCl, pH 9.0, containing urea in concentrations which decreased with each change: 4 M, 2M, 1 M, and finally no urea. The final dialysis was into 0.25 mM sodium bicarbonate, 0.21 mM sodium carbonate ("1% CB"). Aggregated Δ9(Ser)bGH was removed by ultrafiltration through a 100,000 dalton cut-off membrane under 15 psi of nitrogen, monomeric Δ9(Ser)bGH appearing in the filtrate. The filtrate was concentrated to a final protein concentration of 1-2 mg/ml by ultrafiltration on a 5,000 dalton cut-off membrane and lyophilized. The final product contained 14 mg of Δ9(Ser)bGH which was >95% pure by gel analysis. The overall yield was 6% with respect to the original Δ9(Ser)bGH titer in the fermentor.

EXAMPLE II

Purification and Activation of Δ9(Ser)bGH

Inclusions were prepared as described in Example I from a different fermentor run. One gram of these inclusions was extracted into 100 volumes of 60 mM ethanolamine-HCl, 1% SDS, 1 mM EDTA, by stirring overnight. Because solubilization was incomplete, residual insoluble material was removed by centrifugation at 10,000 ×g for 30 minutes. The dialysis and urea treatment steps were performed as described in Example I. The urea-treated extract was chromatographed on a 5×43 cm column of QAE-Sephadex A-25 in 60 mM ethanolamine-HCl, pH 9.0, 6 M urea, at 100 ml/hr flow rate. The fractions containing Δ9(Ser)bGH were pooled and diluted 1:1 with buffer without urea to reduce the urea concentration to 3 M. The diluted solution was then dialyzed directly into 25 mM NaHCO$_3$ and 21 mM Na$_2$CO$_3$ (CB) containing 1 mM EDTA. Aggregates were removed by chromatographing the dialyzed material on a 4.4×15 cm column of DEAE-Trisacryl in CB/1 mM EDTA. Monomeric Δ9(Ser)bGH eluted in the breakthrough fractions; these were pooled, concentrated threefold by ultrafiltration on a 5000 dalton cut-off membrane, extensively dialyzed against 1% CB to reduce the salt content of the final product, concentrated an additional sixfold, and lyophilized. The final product contained 62 mg of Δ9(Ser)bGH which was 90% pure. The overall yield based upon the Δ9(Ser)bGH content of the inclusion bodies was 17%.

EXAMPLE III

Purification and Activation of Δ7pGH

Inclusion bodies were obtained from *E. coli*, IMC No. 2 (ATCC 53031), which had been cultured under Δ7pGH-producing conditions, in the same manner as described in Example I. Ten grams of these inclusions were extracted into 30 volumes of 60 mM ethanolamine-HCl, pH 9.0, 1% SDS, 10 mM 2-mercaptoethanol, by stirring overnight. The extract required centrifugation at 20,000 ×g for 60 minutes to remove residual insolubles. It was then dialyzed against 30 volumes of 60 mM ethanolamine-HCl, pH 9.0. Because of a high Δ7pGH content which might cause increased aggregation, the extract was diluted 1:1 with 60 mM ethanolamine-HCl, pH 9.0, 20% glycerol. This material was treated with solid urea to a final concentration of 6 M and was incubated for 30 minutes at room temperature. The treated extract was then loaded onto a 5×43 cm column of QAE-Sephadex A-25 equilibrated with 60 mM ethanolamine-HCl, pH 9.0, 6 M urea, 10% glycerol, and was eluted with the same buffer. The Δ7pGH eluted in the void volume of the column. The fractions containing Δ7pGH were pooled. Removal of urea was effected by immersing a dialysis bag containing the Δ7pGH solution into a flask containing the column elution buffer and then slowly pumping out the buffer while pumping in a solution of CB+10% glycerol from an external reservoir at the same rate. When the external reservoir became empty, it was refilled with 1% CB without glycerol and the procedure was repeated. The dialyzed material was then ultrafiltered through a 100,000 dalton cut-off membrane under 15 psi of nitrogen. The filtrate containing monomeric Δ7pGH was concentrated roughly 20-fold by ultrafiltration over a 5000 dalton cut-off membrane and was lyophilized. The final product contained 17 mg of Δ7pGH which was >95% pure by gel analysis. Overall yield was 2% based upon the pGH content of the original extract.

What is claimed is:

1. A method for purifying and solubilizing a protein that is produced as an insoluble, impure inclusion body in a transformant microorganism which consists essentially of:
  (a) extracting the inclusion bodies into a buffered solution of sodium dodecyl sulfate to solubilize the protein;
  (b) treating the sodium dodecyl sulfate and protein with urea to insure that SDS can be removed from the protein solution by anion-exchange chromatography;
  (c) removing the sodium dodecyl sulfate and purifying the protein by chromatographing the solution obtained in step (b) on an anion-exchange column; and
  (d) dialyzing the solution obtained from the anion-exchange column, thereby removing the urea and allowing the protein to refold into its native conformation.

2. A method as claimed in claim 1, wherein the sodium dodecyl sulfate solution has a concentration from about 0.5% to 5.0%.

3. A method as claimed in claim 1, wherein the sodium dodecyl sulfate solution has a concentration of about 1%.

4. A method as claimed in claim 1, wherein the sodium dodecyl sulfate solution contains ethanolamine in a concentration from about 0.02 M to 0.10 M.

5. A method as claimed in claim 1, wherein the sodium dodecyl sulfate solution has a pH from about pH 8.5 to about pH 10.5.

6. A method as claimed in claim 1, wherein the protein-SDS solution is treated with solid urea to a final urea concentration from about 4 M to about 10 M.

7. A method as claimed in claim 1, wherein the protein-SDS solution is treated with solid urea to a final urea concentration of about 6 M.

8. A method as claimed in claim 1, wherein the urea-treated protein-SDS solution which is chromatographed on the anion-exchange column has a pH from about pH 7.5 to pH: 9.5.

9. A method as claimed in claim 1, wherein the anion-exchange resin comprises cationic groups attached to a polysaccharide support selected from the group consisting of dextran, agarose and cellulose.

10. A method as claimed in claim 1, wherein the anion-exchange resin contains cationic groups which retain substantially all their positive charge at a pH above pH 9.0.

11. A method as claimed in claim 1, wherein the anion-exchange resin comprises cationic groups of the formula $-CH_2CH_2N^+(CH_2CH_3)_2CH_2CH(OH)CH_3$ attached to a polysaccharide support selected from the group consisting of dextran, agarose and cellulose.

12. A method as claimed in claim 1, wherein the anion-exchange resin is a packed column of QAE-Sephadex A-25.

13. A method as claimed in claim 1, wherein the protein is eluted from the anion-exchange column using an eluent selected from buffered urea solutions at alkaline pH.

14. A method as claimed in claim 1, wherein the protein is an animal growth hormone.

15. A method as claimed in claim 14, wherein the animal growth hormone is bovine growth hormone or a biologically active fragment or analog thereof.

16. A method as claimed in claim 14, wherein the animal growth hormone is porcine growth hormone or a biologically active fragment or analog thereof.

17. A method as claimed in claim 15, wherein the animal growth hormone is Δ9(Ser)bGH.

18. A method as claimed in claim 16, wherein the animal growth hormone is Δ7pGH.

19. A method for purifying, solubilizing and activating a protein that is produced as an insoluble, impure, biologically inactive inclusion body in a transformant microorganism which consists essentially of:
  (a) extracting the inclusion body into a buffered solution of sodium dodecyl sulfate to solubilize the protein;
  (b) treating the solution of sodium dodecyl sulfate and protein with urea to insure that SDS can be removed from the protein solution by anion-exchange chromatography;
  (c) removing the sodium dodecyl sulfate and purifying the protein by chromatographing the solution obtained in step (b) on an anion-exchange column;
  (d) dialyzing the solution obtained from the anion-exchange column, thereby removing the urea and allowing the protein to refold into its native conformation; and
  (e) activating the protein solution by removing soluble protein aggregates from the solution.

20. A method as claimed in claim 19, wherein the soluble protein aggregates are removed by ultrafiltration.

21. A method as claimed in claim 19, wherein the soluble protein aggregates are removed by loading the solution obtained in step (d) onto a weak anion-exchange resin under conditions in which the protein aggregates bind to the resin but monomeric protein does not bind to the resin and collecting the unbound portion of the solution.

22. A method as claimed in claim 21, wherein the weak anion-exchange resin comprises cationic groups that lose positive charge at a pH above pH 9.0 bound to a solid support selected from dextrose, agarose, sepharose and Trisacryl.

23. A method as claimed in claim 22, wherein the cationic groups are diethylaminoethyl groups.

24. A method as claimed in claim 21, wherein the weak anion-exchange resin is DEAE-Trisacryl.

25. A method as claimed in claim 21, wherein the protein solution which is loaded onto the weak anion-exchange resin has a pH from about 9.0 to 10.0.

* * * * *